(12) United States Patent
Xu et al.

(10) Patent No.: US 8,795,708 B2
(45) Date of Patent: Aug. 5, 2014

(54) TREATING DEFECTIVE DURA WITH SYNTHETIC ARTIFICIAL DURA SUBSTITUTE

(75) Inventors: Tao Xu, Guangdong (CN); Yuyu Yuan, Guangdong (CN)

(73) Assignee: Medprin Regenerative Medical Technologies Co., Ltd., Guangzhou (CN)

( * ) Notice: Subject to any disclaimer, the term of this patent is extended or adjusted under 35 U.S.C. 154(b) by 5 days.

(21) Appl. No.: 13/255,356

(22) PCT Filed: Feb. 8, 2010

(86) PCT No.: PCT/CN2010/070566
§ 371 (c)(1),
(2), (4) Date: Oct. 18, 2011

(87) PCT Pub. No.: WO2010/102533
PCT Pub. Date: Sep. 16, 2010

(65) Prior Publication Data
US 2012/0029654 A1 Feb. 2, 2012

(30) Foreign Application Priority Data

| Mar. 10, 2009 | (CN) | 2009 1 0037736 |
| Mar. 10, 2009 | (CN) | 2009 1 0037739 |
| May 22, 2009 | (CN) | 2009 1 0039687 |

(51) Int. Cl.
*A61F 2/00* (2006.01)
(52) U.S. Cl.
USPC ........................................................ 424/423
(58) Field of Classification Search
None
See application file for complete search history.

(56) References Cited

U.S. PATENT DOCUMENTS

| 4,043,331 | A | 8/1977 | Martin et al. | |
| 6,514,291 | B1 | 2/2003 | Yamauchi et al. | |
| 6,753,454 | B1 * | 6/2004 | Smith et al. | 602/41 |
| 2007/0233275 | A1 | 10/2007 | Shirahama et al. | |
| 2010/0129450 | A1 * | 5/2010 | Atala et al. | 424/486 |

FOREIGN PATENT DOCUMENTS

| CN | 1274292 A | 11/2000 |
| CN | 1317297 A | 10/2001 |
| CN | 101036802 A | 9/2007 |
| CN | 101347403 A | 1/2009 |
| CN | 101507661 A | 8/2009 |
| CN | 101559242 A | 10/2009 |
| CN | 101559327 A | 10/2009 |
| WO | WO 2009/022230 | 2/2009 |

OTHER PUBLICATIONS

CN 101036802 machine translation, translated 2013.*
CN 1317297 machine translation, translated 2013.*
Reina et al., Acta Anaesth Belg 60: 7-17 (2009).*
Kumar et al., Advanced Drug Delivery Reviews 54: 889-910 (2002).*
He et al., Iranian Polymer J 19: 625-633 (2010).*
Parlato et al., "Dural reconstruction in meningioma surgery," in Meningiomas—Management and Surgery, Dr. Daniel Monleon (Ed.), ISBN: 978-953-51-0175-8, InTech, 136 pages, (2012).
Chappell et al., "Gore Preclude MVP dura substitute applied as a nonwatertight "underlay" graft for craniotomies: product and technique evaluation," Surgical Neurology, vol. 71, No. 1, pp. 126-129 (Jan. 2009).
Shih et al., "Synthesis, Characterization and Evaluation of Segmented Polycaprolactone for Development of Dura Substitute," Procedia Engineering, 36:144-9 (2012).
International Search Report PCT/CN2010/070566 dated Apr. 20, 2010.

* cited by examiner

*Primary Examiner* — Abigail Fisher
*Assistant Examiner* — Thor Nielsen
(74) *Attorney, Agent, or Firm* — Foley & Lardner LLP; Steven A. Bent; Alex Y. Nie

(57) ABSTRACT

Disclosed are an artificial dura mater and manufacturing method thereof. The artificial dura mater includes electrospun layers prepared by electrostatic spinning, at least one of which is a hydrophobic electrospun layer. Further, above the hydrophobic electrospun layer, there can be at least one hydrophilic electrospun layer. A transition layer can be further included between the hydrophobic and the hydrophilic electrospun layers. Additionally, cytokines and/or medicines can be affixed to either or both of the hydrophobic and the hydrophilic electrospun layers, by way of bio-printing. The disclosed artificial dura mater shows good biocompatibility, enhances dural tissue regeneration, achieves excellent repairing effects, prevents adhesion, allows complete absorption, has good mechanical properties, ensures low infection rates, and can be loaded with therapeutic agents.

11 Claims, 6 Drawing Sheets

TREATING DEFECTIVE DURA WITH SYNTHETIC ARTIFICIAL DURA SUBSTITUTE

CROSS-REFERENCE TO RELATED APPLICATIONS

This application is a national stage application under 35 U.S.C. §371 of International Application No. PCT/CN2010/070566, filed Feb. 8, 2010, which in turn claims the benefit of Chinese Applications No. 200910037736.5, filed on Mar. 10, 2009, No. 200910037739.9, filed on Mar. 1, 2009, and No. 200910039687.9, filed on May 22, 2009.

TECHNICAL FIELD

The invention is directed to artificial biofilms, in particular artificial dura maters, and to related manufacturing methodology.

BACKGROUND

Dural defect is a common problem during neurosurgery. Open craniocerebral injuries (industrial, traffic or war-related), tumor invasion, congenital meninges defects or other cranial diseases can lead to defects of the dura mater. Such defects of the dura mater need be repaired timely so as to prevent leakage of the cerebrospinal fluid, encephalocele, and stress from the barometric pressure. Otherwise, it can be life endangering.

Currently, although there are many dura substitutes, materials used in the substitutes can be generally classified into four types: autologous fascia, allograft, natural or synthetic substance, and xenograft. However, clinical application of these materials unavoidably leads to problems such as high infection rates. According to statistics, the infection rate for craniotomy is 4%; the dura mater made of pig's small intestine mucosa gives an infection rate of 3.4%; and the dura mater manufactured by collagen exhibits an infection rate at 3.8%. Because of the blood brain barrier, once intracranial infection occurs, the encephalic plasma concentration of anti-infection drugs can hardly reach the desired level and control of infection becomes difficult. Also, the existing artificial dura products do not have the capability of supplying medicines into the meninges. Therefore, post-operation infection control is often ineffective.

Moreover, one of the common reasons for dural repair with dura mater transplant is damages to the meninges due to tumor invasion. More than half of brain tumors cannot be completely removed by surgery and thus chemotherapy is necessary after the surgery. Many chemotherapeutic drugs are toxic and cannot pass the blood brain barrier, so that an effective concentration of the drugs cannot be reached resulting in diminished chemotherapy effects.

Current artificial dural substitute products usually do not contain therapeutic drugs of interest. For instance, due to the dense structures, the autologous fascia can not be loaded with drugs naturally, and it is difficult to load drugs into allograft or xenograft. However, due to their good malleability, synthetic material-based dural substitutes can be readily loaded with drugs. On the other hand, due to the limitation of loading methods of a drug, it is also not easy to load the drug onto artificial dura mater, and yet allow release of the drug upon transplantation to achieve therapeutic objectives. To date, the common way to load an anti-infection drug onto an artificial dura mater substitute is to soak the substitute with the drug. With this method, most of medicine remains on the surface of artificial dura mater, which is easily lost, making it difficult to achieve controlled release.

It is apparent, therefore, that current artificial dura mater substitutes have shortcomings. Among these are a high infection rate, poor bio-compatibility, incomplete absorbability, and difficulty in loading medicine and controlling the effective release of the medicine.

SUMMARY OF THE INVENTION

In view of these disadvantages of conventional technology, the present invention provides an artificial dura mater that is characterized by excellent tissue compatibility, ideal anti-adhesion, complete absorption, good mechanical properties, a low infection rate, and a capability to load a variety of therapeutic substances. An artificial dura mater of the invention is comprised of electrospun layers, including at least one hydrophobic electrospun layer. The invention contemplates employing methodology that comprises elctrospinning to prepare such a layer with one or more hydrophobic polymers.

Suitable hydrophobic polymers can be selected for this purpose from the group consisting of hydrophobic aliphatic polyester, polyetherester, polyorthoester, polyurethane, polyanhydride, polyphosphazene, and polyamino acid, and copolymers and mixtures thereof. Thus, the hydrophobic aliphatic polyester can be at least one selected from the group consisting of polylactic acid, polyglycolide, polycaprolactone, and polyhydroxybutyrate (PHB). The polyetherester can be at least one selected from the group consisting of the polydioxanone (PDO), glycol/lactic acid copolymer, and glycol/butylenes terephthalate copolymer. The polyanhydride is at least one selected from the group consisting of poly(sebacic acid-hexadecanedioi acid anhydride), type-I polyanhydride, type-II polyanhydride, type-III polyanhydride and type-IV polyanhydride.

The hydrophobic layer-containing artificial dura mater has a strength similar to that of human dura mater. It can seal and protect a person's brain and prevent leakage of the cerebrospinal fluid before a person's own dura mater is regenerated. The hydrophobic layer does not allow cells' migration or attachment and thus can achieve an anti-adhesion effect. In practice, more than one hydrophobic layers can be included to provide different levels of strength Furthermore, in the artificial dura mater according to the invention, at least a hydrophilic electrospun layer can be placed on the hydrophobic electrospun layer. The hydrophilic layer can be prepared by electrospinning with one or more types of hydrophilic polymers selected from the group consisting of chondroitine sulfate, heparin, agar, glucan, algin, cellulose, modified cellulose, alginate, starch, gelatin, fibrinogen, silk protein, elastin-mimicry peptide polymer, collagen, chitosan, modified chitosan, hydrophilic polyurethane, polyethylene glycol, polymethylmethacrylate, PHBV, PHBHHx, polyvinyl alcohol, and polylactide, and mixtures thereof.

When the dura mater is transplanted into the brain, the hydrophobic layer is placed proximate to the brain surface to take advantage of its anti-adhesion capability; whereas the hydrophilic layer, which serves as an excellent nanofiber scaffold for the adhesion, migration, proliferation, and differentiation of cells, is placed distant to the brain. As the hydrophilic layer is prepared with hydrophilic materials of good bio-compatibility, it can effectively enhance the migration and proliferation of stem cells and fibroblasts, and consequently promote the growth of autologous dura mater. In practice, the hydrophilic layer can include more than one layer, so as to satisfy different needs.

According to one embodiment of the invention, the artificial dura mater also can have a transition layer between the hydrophobic and hydrophilic layers. The transition layer is prepared by an electrospinning method comprising with one or more polymers, and it has hydrophilicity that gradually increases from the side proximate to the hydrophobic electrospun layer to the side proximate to the hydrophilic electrospun layer. The present of the transition layer can improve the affinity between the hydrophobic and hydrophilic layers.

According to another embodiment of the invention, any one or more of the hydrophobic layers, the hydrophilic layers, and the transition layers can be blended with a cytokine and/or a medicine. Such layers can allow release of the cytokine and/or the medicine into local brain tissue upon transplantation, along with the absorption of the polymers. The cytokine and/or the medicine released to the local brain tissue can then be useful in preventing local infection, adhesion, and/or tumor's recrudesce, or promoting the restoration of autologous dura mater.

According to yet another embodiment of the invention, the hydrophobic layer and/or the hydrophilic layer can be affixed with the cytokine and/or the medicine. In this regard, the cytokine can be an agent that plays a role in adhesion, migration, proliferation, and/or differentiation of fibroblast. Thus, it can be selected from the group consisting of interleukin, colony stimulating factor, tumor necrosis factor, platelet derived growth factor, basic fibroblast factor, and combinations thereof. The cytokine can facilitate the recovery of the defective dura mater.

A medicine used in accordance with the invention can be one or more selected from the group consisting of antibiotic, hemostat, anti-adhesion agent, and tumor-resistance drug. These medicines can be placed onto the artificial dura mater, based on actual needs. Once the artificial dura mater is transplanted, the medicines are released gradually to local brain tissues, thereby bypassing the blood brain barrier, to achieve therapeutic effects during the degradation of the polymers and regeneration of the dural defect.

Furthermore, the cytokine and/or medicine can be enclosed in a hydrogel. With the adhesion and fixation effects of hydrogel, the medicine can, depending on the local situation, be uniformly or specifically released. The hydrogel can be prepared with one or more selected from the group consisting of polysaccharide polymer, polypeptide polymer, and synthetic hydrophilic high molecular polymer.

According to one embodiment of the invention, the hydrophobic electrospun layer of the artificial dura mater is comprised of fibers having a diameter of 50-1000 nM. According to one embodiment of the invention, the hydrophobic electrospun layer has pores of a size of less than 3 µM, whereas the fibers of the hydrophilic electrospun layer have a diameter of 5-200 µM, and a pore size of 20-200 µM. The pore size depends largely on the diameter of the fibers. When the diameter of fiber decreases, the pore size reduces. Thus, by controlling the fiber's diameter, one can control the pore size of the electrospun layer as well. The average diameter of a human cell is 10-50 µM. The meninges mainly consist of the fibroblasts and collagen fibers excreted from fibroblast. Most of the fibroblasts have a diameter of 20-30 µM. The pore size of the hydrophobic layer is less than 3 µM, which can therefore prevent the entry of cells and adhesion between dura mater and brain tissue. The hydrophilic layer has a pore size equal to or larger than the average diameter of cell, which can promote the entry and migration of cell.

According to further aspect of the invention, a method for preparing an artificial dura mater is also provided, comprising the following steps:

A) dissolving a hydrophobic polymer into a solvent to obtain a hydrophobic electrospinning solution, wherein the hydrophobic polymer is selected from the group consisting of hydrophobic aliphatic polyester, polyetherester, polyorthoester, polyurethane, polyanhydride, polyphosphazene, polyamino acid and copolymers and the mixtures thereof;

B) producing, by electrospinning, a film-like (or fleece-like) hydrophobic electrospun layer from the hydrophobic electrospinning solution, thereby preparing the artificial dura mater.

Further, the hydrophobic aliphatic polyester can be at least one selected from the group consisting of polylactic acid, polyglycolide, polycaprolactone and polyhydroxybutyrate. The polyetherester can be at least one selected from the group consisting of polydioxanone (PDO), glycol/lactic acid copolymer and glycol/butylenes terephthalate copolymer. The polyanhydride can be at least one selected from the group consisting of poly(sebacic acid-hexadecanedioi acid anhydride), type I polyanhydride, type II polyanhydride, type III polyanhydride and type IV polyanhydride.

The method, applying the principle of electrospinning, forms the artificial dura mater by using a particular polymer. The dura mater can effectively prevent it from adhering to brain tissue.

To further prevent the adhesion of artificial dura mater to brain tissue, the diameter of fibers can be controlled, such that the pore size of the scaffold is also controlled. In this respect, the artificial dura mater inhibits cell migration. The diameter of fibers of the hydrophobic electrospun layer can be controlled within 50-1000 nM. According to one embodiment of the invention, the pore size of hydrophobic electrospun layer is less than 3 µM.

In the method described above, at step B), the electrospinning is preformed with a micro-injection pump operated at a velocity of 0.1-5.0 milliliters/hour and a. high voltage generator operated at a voltage of 5-40 kilovolts and with a receiving distance of 5.0-30.0 centimeters.

To achieve a better effect in clinical therapy, the invention also provides a method, alike to electrospinning, to form a hydrophilic electrospun layer on the hydrophobic layer that comprising the steps of:

a') Dissolving a hydrophilic polymer into solvent to obtain a hydrophilic electrospinning solution, wherein The hydrophilic polymer is selected from the group consisting of chondroitine sulfate, heparin, agar, glucan, algin, modified cellulose, alginate, starch, cellulose, gelatin, fibrinogen, silk protein, elastin-mimicry peptide polymer, collagen, chitosan, modified chitosan, hydrophilic polyurethane, polyethylene glycol, polymethylmethacrylate, PHBV, PHBHHx, polyvinyl alcohol polylactide.

b') Placing the hydrophilic electrospinning solution, by electrospinning, on the hydrophobic layer to form the hydrophilic electrospun layer.

The hydrophilic electrospun layer is placed distant to the brain surface, in order to promote migration of cells and regeneration of dural mater. To facilitate the entry of cell, the hydrophilic electrospun layer has fibers with a diameter of 5-200 µM and pores of a size of 20-200 µM.

In step b'), the formation of hydrophilic electrospun layer, the electrospinning is preformed with a micro-injection pump operated at a velocity of 0.1-20.0 milliliters/hour and a high voltage generator operated at a voltage of 10-40 kilovolts and with a receiving distance of 5.0-30.0 centimeters.

In the process of electrospinning, generally, the hydrophobic and hydrophilic polymers should be dissolved into appropriate solvents respectively, to form electrospinning solutions. Often, the solvents are volatile organic solvents which include but not limited to methanoic acid, acetic acid, ethyl alcohol, acetone, dimethyl formamide, dimethyl acetamide, tetrahydrofuran, dimethyl sulfoxide, hexafluoro isopropyl alcohol, trifluoroethyl alcohol, dichloromethane, trichloromethane, methyl alcohol, ethyl alcohol, chloroform, dioxane, trifluoroethane, trifluoroacetic acid and mixtures thereof. The volatile organic solvents will quickly volatilize during the process of forming electrospun layers, and the final electrospun layers will contain no or little residual organic solvent which can be removed in the later steps. In some cases, water can be used as solvent and removed by oven or natural dryness after the electrospun layers are formed.

Furthermore, the method for preparing an artificial dura mater provided in present invention further comprises, before the hydrophilic electrospun layer is prepared, forming a transition layer by electrospinning between the hydrophilic and hydrophobic layers, wherein the transition layer has hydrophilicity that gradually increase from the side proximate to the hydrophobic electrospun layer to the side proximate to the hydrophilic electrospun layer. The materials, solvents and electrospinning parameters for preparing the transition layer can be determined based on the actual situation and need. The present of the transition layer can improve the hydrophilicity between hydrophilic and hydrophobic layers.

In one embodiment of the invention, during the formation of each electrospun layer by electrostatic spinning, a cytokine and/or a medicine can be added to the corresponding electrospinning solutions. With the blending technique, the blended layers of polymers and a cytokine and/or a medicine have a better satisfaction for clinic application and a better therapeutic effect.

The method for preparing an artificial dura mater provided in present invention further comprises, by bio-printing, forming a distribution of a cytokine and/or a medicine on the hydrophobic electrospun layer and/or the hydrophilic electrospun layer. Bio-printing is a technology for printing a cytokine and/or a medicine onto bio-papers that comprising scaffolds of the hydrophobic electrospun layers and/or the hydrophilic electrospun layers.

To make the cytokine and/or medicine distribute evenly and point fixed onto the layers, the cytokine and/or medicine can be enclosed into a hydrogel.

Specifically, the bio-printing comprises the steps of:

a") admixing a hydrogel solution with cytokine and/or medicine to form a solution; and b") printing the solution onto the hydrophobic electrospun layers and/or hydrophilic electrospun layers using a bio-printing technology.

The hydrogel solution in the invention comprises the aqueous solutions of polysaccharide polymer, polypeptide polymer synthetic hydrophilic polymer or mixtures thereof. Wherein the polysaccharide polymer includes but not limited to starch, cellulose, alginate, hyaluronic acid and chitosan. The polypeptide polymer includes but not limited to collagen, poly-L-lysine and PLGA. The synthetic hydrophilic polymer includes but not limited topolyacrylic acid, polymethacrylic acid, polyacrylamide and N-isopropyl acrylamide.

The hydrogel is liquid under normal circumstances. At appropriate temperature or under specific conditions, it can turn to gel for a short time by which it has a good adhesion. According to the invention, some hydrogels need a cross-linking agent in participation of reaction. Therefore, the method further comprises, before bio-printing, a pretreatment of the hydrophobic and/or hydrophilic layers with a solution comprising a cross-linking agent. With the pretreatment by the solution comprising a cross-linking, a cross-linking agent is adhere on the layer or layers. After that, a cytokine and/or a medicine will be added into a hydrogel solution, and the mixed solution will be placed into the printer head. While printing, when the hydrogel solution with cytokine and/or medicine reaches the electrospun layers, it solidifies and adheres to the layers.

In a uniform and stable printing the cytokine and/or medicine can be evenly released. While in a customized printing with varied speeds and locations for an individual case, the cytokine and/or medicine can be released in specific area. The selection of cross-linking agent is based on the type of hydrogel. For instance, while the hydrogel is sodium alginate, the cross-linking agent is calcium chloride; while the hydrogel is fibrinogen, the cross-linking agent is thrombin.

Compared with the prior arts, the invention exhibits the following advantages:

(1) Its mechanical properties satisfy the requirement for tensile strength and flexibility, and it is waterproof and anti-adhesion;

(2) The materials comprising of the membranes is free from poison and harmless to human body, have good compatibility, allow completely absorption after implantation, which avoids the occurrence of tumor or cancer;

(3) The membrane is not prepared with ingredients derived from biological sources, therefore it can avoid risks such as immune rejection, virus spreading and disease infectiousness;

(4) The designed double layers can prevent adhesion, promote the growth of autologous cells, which, enable an earlier restoration of dura mater;

(5) By incorporating the bio-printing technology, the therapeutic substances can be introduced into the membrane and can be released in a controlled manner after the implantation;

(6) The materials are abundant in source and, cheap in cost and convenient in transportation and store;

(7) The preparing method comprises easy procedures, costs low, and is easy for industrialized development; and (8) The clinical application is simple, and a patient customized application is also available.

The additional aspects or advantages of the invention will be further given in the following descriptions, and part of them will become obvious through the following descriptions or be understood more easily through the practice.

BRIEF DESCRIPTION OF THE DRAWINGS

The above and/or additional aspects and advantages or the additional aspects and advantages of the invention will be more obvious and easier for being understood through the following descriptions in conjunction with the drawings and embodiments, wherein.

In the figures, the numbers represent in this way.
1. Electrospinning sprayer;
2. Spinning fibers;
3. High voltage power source;
4. Receiving device;
5. Bio-printer head;
6. Vessel;
7. Hydrophobic spinning thread;
8. Medicine;
9. Hydrophilic spinning fibers;
10. Cytokine or medicine;
11. Spinning fibers of transition layer;
A. Hydrophobic electrospun layer;
B. Hydrophilic electrospun layer;
C. Transition layer.

DETAILED DESCRIPTION

Now, examples of the invention will be explained in detail. The illustration of examples will be shown in the accompanying drawings, in which the same number represents the same or similar elements. The examples described with reference to the drawings are only illustrations, which intend for explaining the invention and do not limit the invention.

With reference to FIGS. 1 to 8, the artificial dura mater and manufacturing methods therefor are described in details below.

Figure 1:
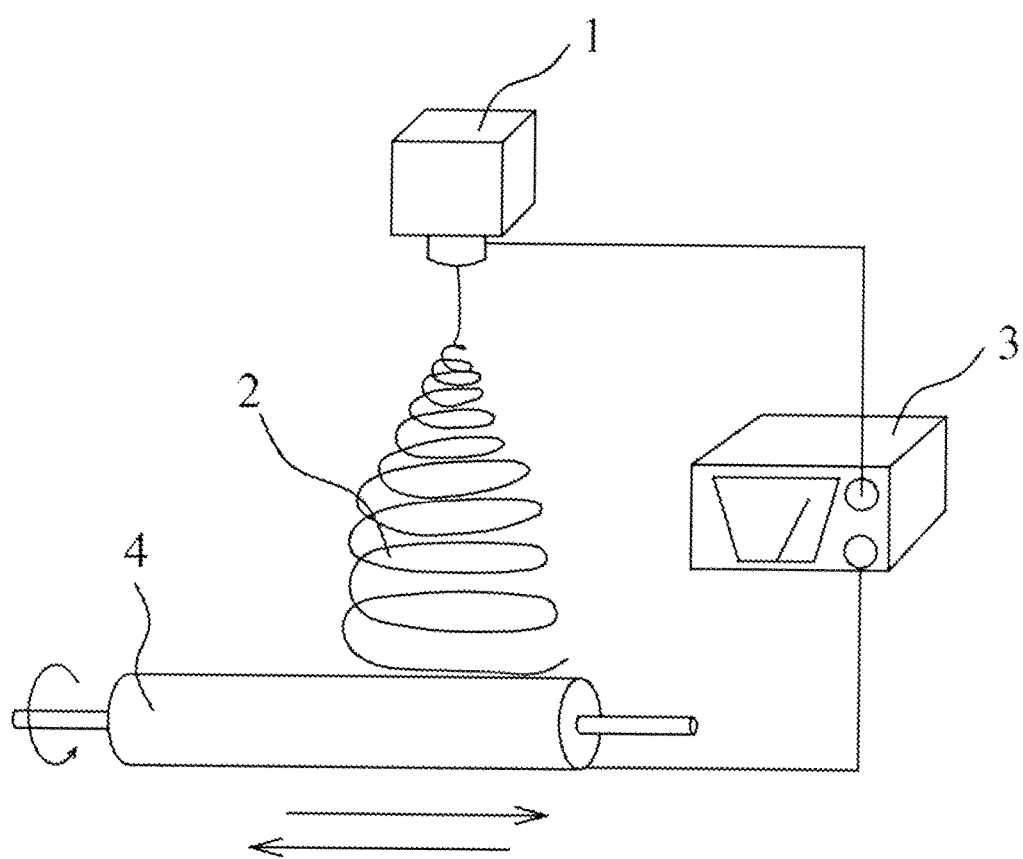
FIG. 1 is an illustration of electrospinning process to prepare the artificial dura mater according to the invention.

An illustration of electrospinning process to prepare the artificial dura mater is shown in FIG. 1, the electrospinning sprayer 1 contains the polymer solution, the high voltage power source 3 has its high voltage end connected to the sprayer 1. The receiving device 4 is in cylinder shape, and can be moved leftwards and/or rightwards, along with the axis of cylinder or the long shaft direction of cylinder. The movement of receiving device 4 can be set with computer program, so that the formed electrospun layer will have equal thickness. In practice, the receiving device can be set as a level-off surface, and through the movement between left and right or fore-and-aft, an even reception can be realized. The receiving device 4 is connected with the low voltage end of high voltage power source 3, so that there is a large voltage difference between the sprayer 1 and receiving device 4.

Before the electrospinning starts, the proper polymer solution for electrospinning should be prepared.

It is an option to choose the solution of hydrophobic polymer for electrospinning, and such solution is prepared by dissolving a hydrophobic polymer into a solvent. Wherein the hydrophobic polymer includes but not limited to the hydrophobic aliphatic polyester (covering polylactic acid, polyglycolide, polycaprolactone, and polyhydroxybutyrate), polyetherester (such as polydioxanone), polyorthoester, polyurethane, polyanhydride (such as poly(sebacic acid-hexadecanedioi acid anhydride)), polyphosphazene, polyamino acid and mixtures thereof.

Depending on the design, if the hydrophilic electrospun layer is needed after the hydrophobic electrospun layer is finished, the solution of hydrophilic polymer for electrospinning should be prepared. Wherein the hydrophilic polymer includes but not limited to the chondroitine sulfate, heparin, agar, glucan, algin, modified cellulose, alginate, starch, cellulose, gelatin, fibrinogen, silk protein, elastin-mimicry peptide polymer, collagen, chitosan, modified chitosan, hydrophilic polyurethane, polyethylene glycol, polymethylmethacrylate, PHBV, PHBHHx, polyvinyl alcohol and polylactide. Based on the actual needs, multiple sprayers 1 may be set, in which the hydrophobic polymer solution and the hydrophilic polymer solution are placed respectively. Or, replace the solution in the sprayer 1 after the hydrophobic layer is made.

The solvent of the solution for electrospinning can be water or a volatile organic solvent which includes but not limited to methanoic acid, acetic acid, ethyl alcohol, acetone, dimethyl formamide, dimethyl acetamide, tetrahydrofuran, dimethyl sulfoxide, hexafluoro isopropyl alcohol, trifluoroethyl alcohol, dichloromethane, trichloromethane, methyl alcohol, ethyl alcohol, chloroform, dioxane, trifluoroethane, and trifluoroacetic acid.

Once the solution for electrospinning is ready, the parameters should be set. After that, the power is on, and the electrospinning device is activated. As the spinning fibers 2 is spun from the sprayer 1, the receiving device 4 will move in prescribed procedures, so as to form the uniform electrospun membrane structure.

The parameters of the process to form the hydrophobic electrospun layer are set as follows: a micro-injection pump operated at a velocity of 0.1-5.0 milliliters/hour and a high voltage generator operated at a voltage of 5-40 kilovolts and with a receiving distance of 5.0-30.0 centimeters. The hydrophobic electrospun layer comprises fibers with a diameter, which can be controlled, ranging from 50 to 1000 μM, and pores of a size of less than 3 μM.

The parameters of the process to form the hydrophilic electrospun layer are set as follows: a micro-injection pump operated at a velocity of 0.1-20.0 milliliters/hour and a high voltage generator operated at a voltage of 10-45 Kilovolts and with a receiving distance of 5.0-30.0 centimeters. The hydrophilic electrospun layer comprises fibers with a diameter, which can be controlled, ranging from 5 to 200 μM and pores of a size of 20-200 μM.

Figure 3:
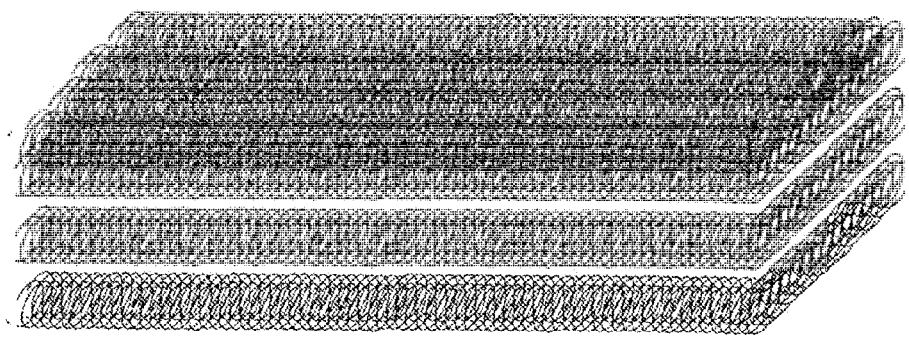
FIG. 3 is an illustration of the artificial dura mater according to the invention comprising the hydrophobic electrospun layer(s).
Figure 4:
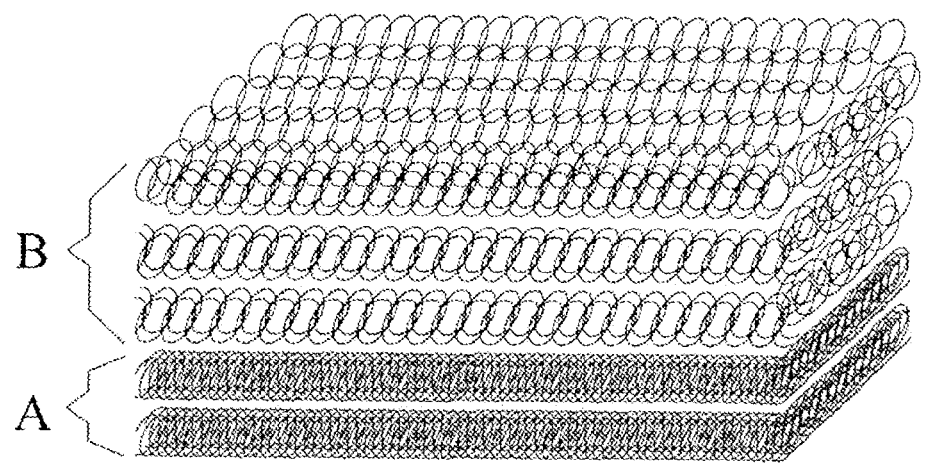
FIG. 4 is an illustration of the artificial dura mater according to the invention comprising the hydrophobic electrospun layer and the hydrophilic electrospun layer.

In practice, the above procedures can be repeated, so as to form multiple hydrophobic layers and/or multiple hydrophilic layers, as shown in FIG. 3 and FIG. 4.

FIG. 3 gives an artificial dura mater with three hydrophobic layers the strength of which is similar to the human's dura mater. As the layers are formed by hydrophobic materials, they are not good for the migration and attachment of cells. Together with the fact that the materials are safe, poison-free and absorbable for human body, they reach the goal of anti-adhesion.

FIG. 4 gives an artificial dura mater consisting of two hydrophobic layers (A) and three hydrophilic layers (B). When the dura mater is transplanted into brain, the anti-adhesive hydrophobic layers (A) are set near to the brain surface, while the hydrophilic layers (B) are set far from the brain surface, providing a fine nanofibrous scaffold for the adhesion, migration, proliferation and differentiation of cells. As the hydrophilic layers are prepared with hydrophilic materials that offers good bio-compatibility and have larger pore size, which is good for the migration of stem cells and fibroblast, consequently, which is favorable for the growth of autologous dura mater.

Once the electrospun layers are made, they will be dried in an oven or in natural manner, dependent on varied solution component. When the solvent of an electrospinning solution is a volatile organic solvent, such as hexafluoro isopropyl alcohol, the procedure for dryness can be omitted since the solvent has completely volatilized while the spinning fibers 2 are spun to the receiving device 4 along with a voltage difference.

As the hydrophobic layer is very different from the hydrophilic layer in the terms of hydrophilicity, the structural stability is not easy to be kept in the application. To solve such problem and increase the hydrophilicity between the two, a transition layer can be applied. The transition layer has a hydrophilicity that gradually increases from the side proximate to the hydrophobic electrospun layer to the side proximate to the hydrophilic electrospun layer. In practice, the electrospinning solution of the transition layer can comprise one or more polymers and corresponding solvent which are determined based on the requirement of hydrophilicity. Then, the solution is placed into the sprayer, by the method the as above, to prepare the transition layer before the hydrophilic layer. The parameters of the process to form the transition layer are set as follows: a micro-injection pump operated at a velocity of 0.1~5.0 milliliters/hour and a high voltage generator operated at a voltage of 5-40 kilovolts and with a receiving distance of 5.0-30.0 centimeters.

Figure 5:
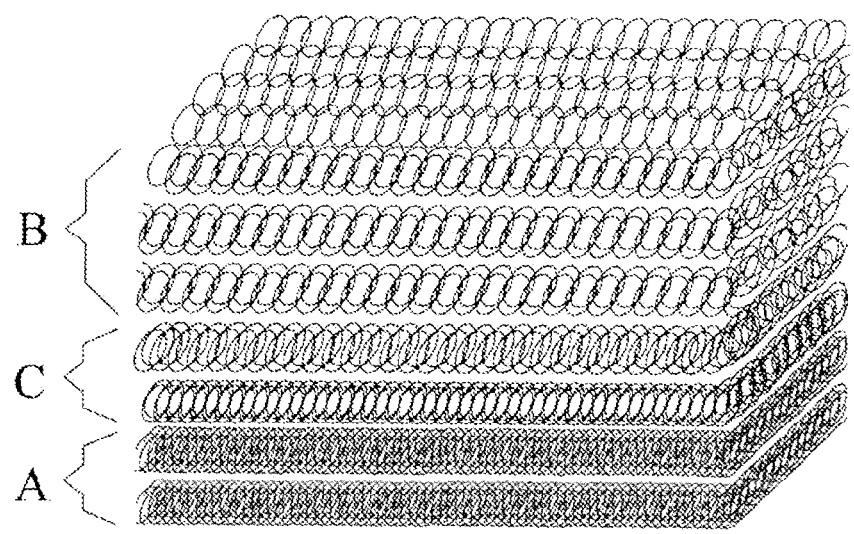
FIG. 5 is an illustration of the artificial dura mater according to the invention comprising hydrophobic layer, hydrophilic layer and transition layer.

The artificial dura mater with transition layer is illustrated in FIG. 5. In the figure, the hydrophobic layer is of two layers, and the hydrophilic layer is of three layers. Between the hydrophobic layers (A) and the hydrophilic layers (B), there is a transition layer of two layers (C), the one, proximate to the hydrophobic layers (A) has a weaker hydrophilicity than the other proximate to the hydrophilic layers.

Figure 6A:
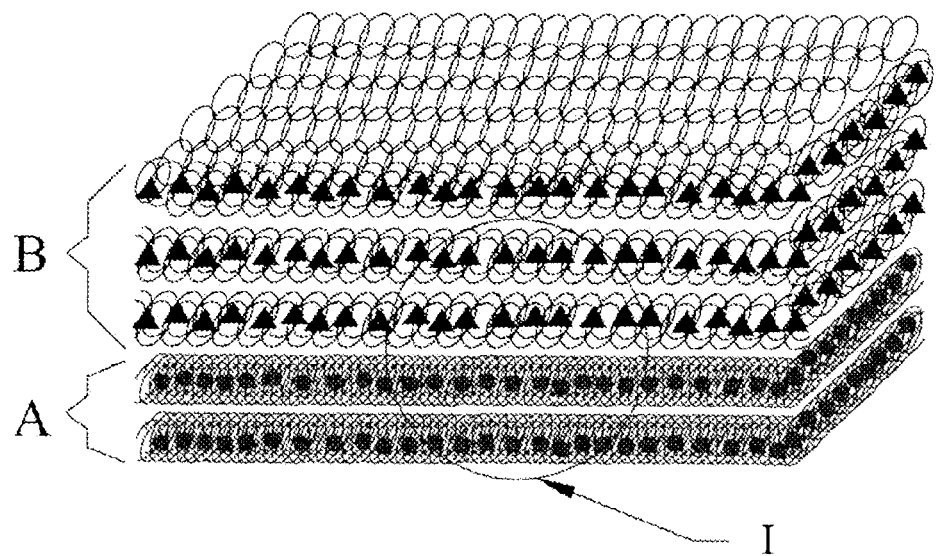
FIG. 6A is an illustration of the blended artificial dura mater according to the invention comprising hydrophobic electrospun layer and hydrophilic electrospun layer
Figure 6B:
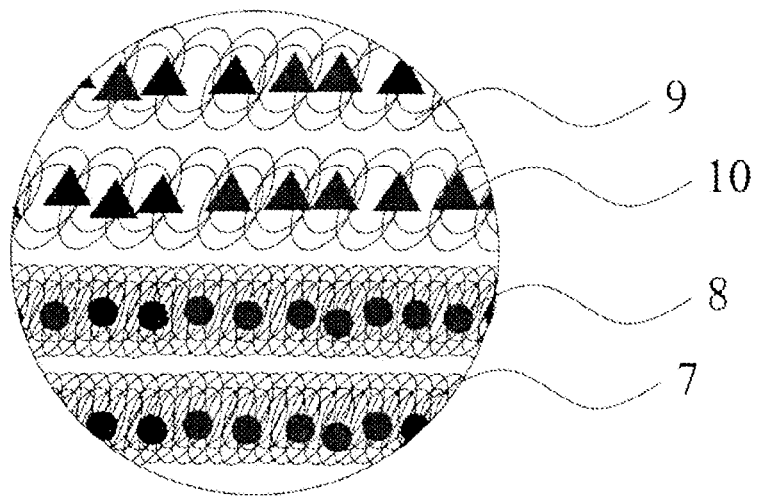
FIG. 6B is a magnified illustration of the Zone I of FIG. 6A.

Furthermore, to realize the addition of cytokine and/or medicine into the artificial dura mater, a blending electrospinning can be adopted. Specifically, a cytokine and/or a medicine can be blended into any one or more layers of the hydrophobic, hydrophilic and transition layers. A cytokine and/or medicine should be put into a corresponding solution. After that, the electrospinning is made and the cytokine and/or medicine will be blended into the spinning fibers 2 as the spinning fibers are formed. The membrane structure will be formed on the receiving device 4. Likewise, this procedure can be repeated. The cytokine and/or medicine added each time can be the same or different. The acquired artificial dura mater is shown in FIG. 6. In FIG. 6A, a hydrophobic layer is of a two-layer structure and a hydrophilic layer is of a three-layer structure. In FIG. 6B, a hydrophobic spinning fiber 7 contains a medicine 8, and a hydrophilic spinning fiber 9 is blended with a cytokine 10.

Figure 7A:
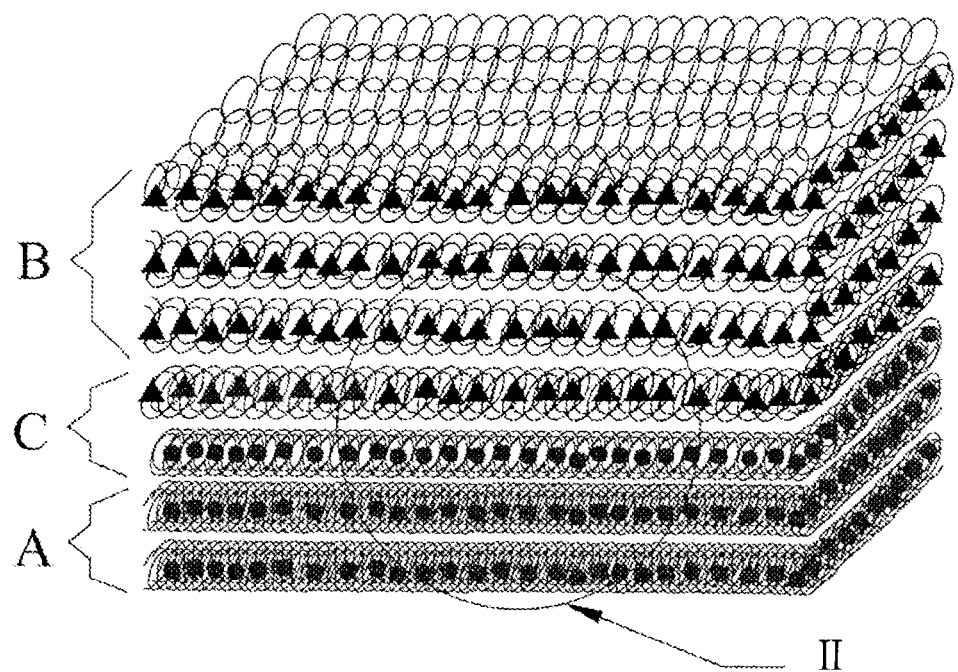
FIG. 7A is an illustration of the blended artificial dura mater according to the invention comprising hydrophobic electrospun layer, hydrophilic electrospun layer and transition layer.
Figure 7B:
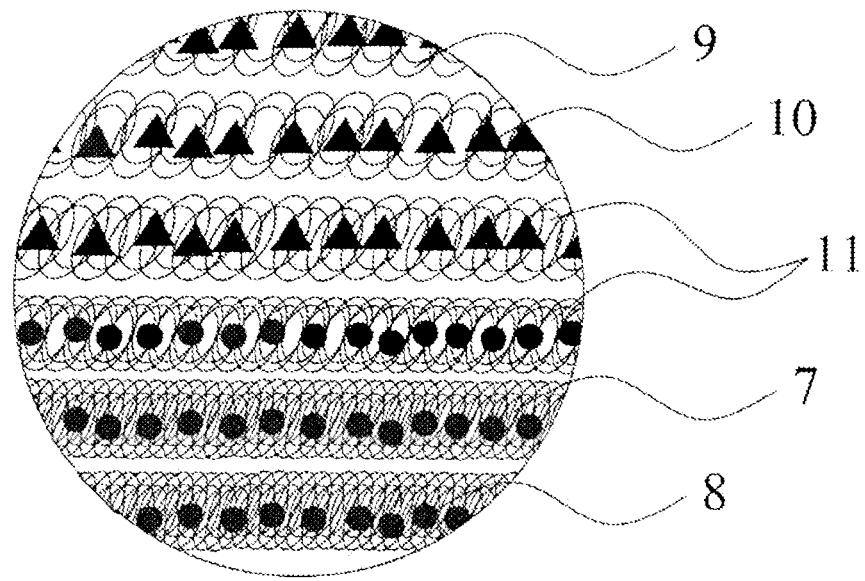
FIG. 7B is an enlarged illustration of Zone II of FIG. 7A.

FIG. 7A has two transition layers C based on FIG. 6. One of them proximate to the hydrophobic layer A, has a weaker hydrophilicity than that proximate to the hydrophilic layer B. From FIG. 7B, the hydrophobic spinning fiber 7 is blended with a medicine 8, and the hydrophilic spinning fiber 9 is blended with a cytokine 10, the spinning fibers of two transition layers 11 is respectively blended with medicine 8 and cytokine 9.

Besides, the invention provides a method that combines electrospinning and bio-printing to prepare artificial dura mater. The bio-printing is an emerging technology, and just have been developed and applied in biomedical fields in recent years. This technology utilizes a special cell solution or a biological active solution as the "bio-ink" and as designed, prints precisely on the spot of a specific substrate (termed as "bio-paper") that can be degraded in the human body. After printing, the bio-papers will be stacked in certain sequence. As the printing technology is used, the bio-ink consisting of cells and/or cytokine can be precisely placed to the designed areas. The bio-papers, if stacked in particular way, will form the three dimensional structure.

Figure 2:
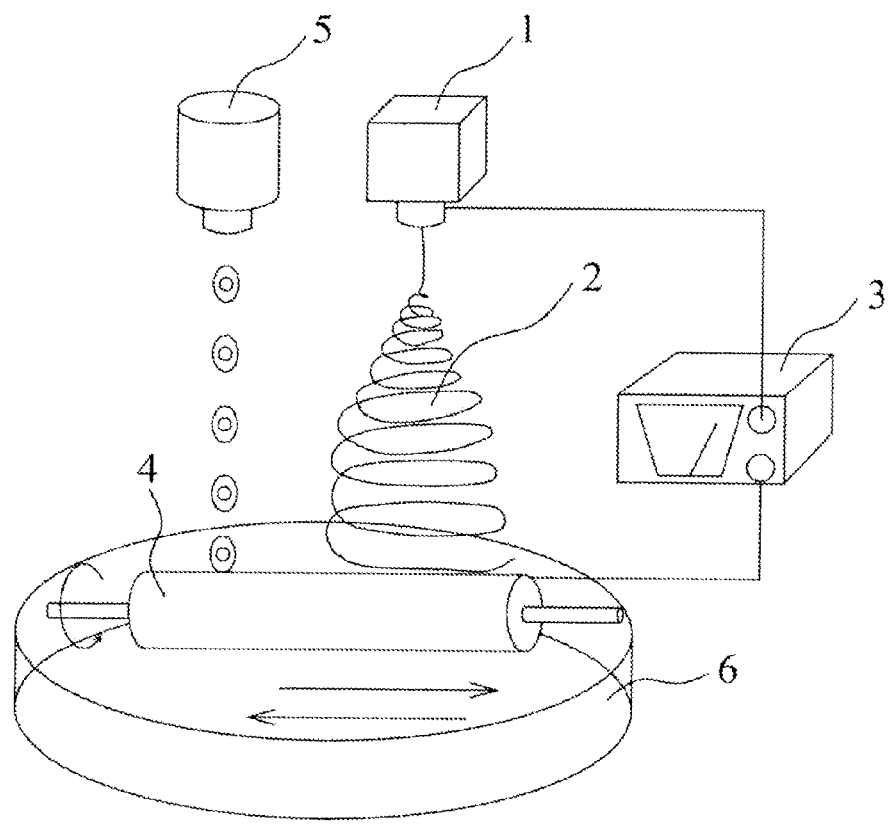
FIG. 2 illustrates of the process for preparing the artificial dura mater according to the invention that combines electrospinning with bio-printing.

The specific implementation is given in FIG. 2. Based on the device given in FIG. 1, the bio-printer head 5 is set, and such head can be obtained by modifying the present commercial inkjet printer as the method, for example, disclosed in U.S. Pat. No. 7,051,654. The head contains a cytokine and/or a medicine. The printing manner and printing position can be set through the computer program in advance. The specific printing procedures can base on the current technologies.

In accordance with one embodiment of the invention, the cytokine and/or medicine can be enclosed in hydrogel. The hydrogel solution can be aqueous solution of polysaccharide polymer, polypeptide polymer or synthetic hydrophilic polymer. The polysaccharide polymer includes but not limited to the starch, cellulose, alginate, hyaluronic acid and chitosan. The polypeptide polymer includes but not limited to the collagen, poly-L-lysine and PLGA. The synthetic, hydrophilic polymer includes but not limited to polyacrylic acid, polymethacrylic acid, polyacrylamide and N-isopropyl acrylamide. The hydrogel is liquid in normal circumstances and becomes gel at certain temperature or under specific conditions. With which, the hydrogel possesses good adhesion, which can make a cytokine and/or a medicine evenly or definitely distribute on the electrostatic spinning layer.

Figure 8A:
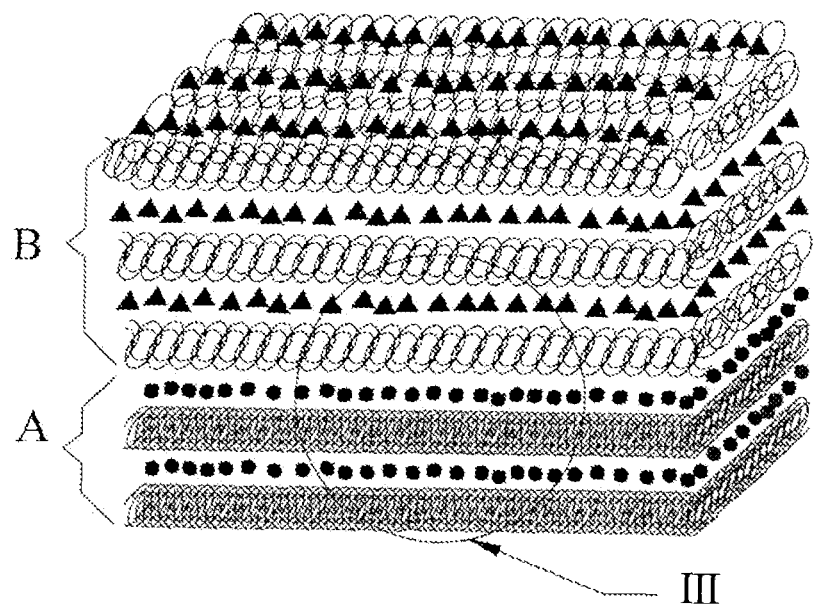
FIG. 8A is an illustration of the artificial dura mater according to the invention obtained combining with bio-printing technology.
Figure 8B:
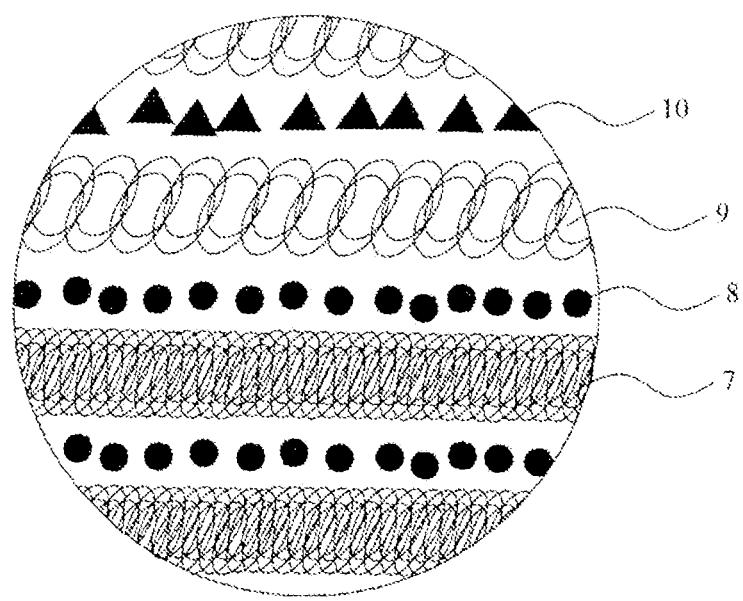
FIG. 8B is an enlarged illustration of Zone III in FIG. 8A.

The procedures of bio-printing with hydrogel are as follows: 1) Put the cytokine and/or medicine, prepared and blended with liquid hydrogel, into the bio-printer head 5. 2) after the electrospun layer is formed, Print on the electrospun layer with jet printer as per the preset program; based on the choice of hydrogel, apply proper conditions to make the hydrogel quickly become gel/jelly that, by offering good adhesion, adhere the cytokine and/or medicine enclosed to the electrospun layers. 3) Set even and uniform distribution of bio-ink and form the artificial dura mater as shown in FIG. 8A, in which, each of hydrophobic layers is printed with a layer of medicine and each of hydrophilic layers is printed with a layer of cytokine. As shown in enlarged FIG. 8B, the film prepared with bio-printing is different from that prepared with blending. A cytokine and/or a medicine are applied on the surface of layers that is formed by the hydrophobic spinning fiber 7 and/or the hydrophilic spinning fiber 9. When such dura mater is transplanted into human body, the cytokine and/or medicine can be evenly released. 4) If necessary, set the concentrated distribution on certain points and make the cytokine and/or the medicine printed into particular areas. When such dura mater is transplanted to the human body, the cytokine and/or the medicine can be mostly released to the wanted specific areas.

The solidification of some hydrogels needs a cross-linking agent to assist. In this case, a bio-printing in the utilization of hydrogel has the following procedures: 1) Put a certain amount of cross-linking agent into the vessel 6. Once the electrospinning starts, the receiving device 4, moving along with the axis or between left and right, will contact the agent, and the formed electrospun layers will adhere with some cross-linking agent 2) Make the bio-printing as given above. When the liquid hydrogel inside the head 5 contacts the cross-linking agent on the electrospun layers, the hydrogel quickly turns to gel/jelly and enables the cytokine and/or medicine enclosed to adhere to the electrospun layers. The selection of cross-linking agent depends on the kind of hydrogel. For instance, when the hydrogel is sodium alginate, the cross-linking agent is calcium chloride; when the hydrogel is fibrinogen, the agent is thrombin.

According to the one embodiment of the invention, the solution of hydrophobic polymer can be hydrophobic poly(L-lactide) (PLLA) and ε-caprolactone dissolved to hexafluoro isopropyl alcohol or dichloromethane, the ratio of the two polymers can be 50:50, 30:70 or 70:30. As a copolymer, the number-average molecular weight is 150,000-500,000. When blending is needed, the hydrophobic solution can be added with 0.01-3% antibiotic solution and/or with 0.001-3% medicine for hemostasis and anti-adhesion. Together with the solution of poly(L-lactide) (PLLA) and ε-caprolactone, the final solution will be obtained.

According to another embodiment of the invention, the solution of hydrophilic polymer can choose hydrophilic polyurethane plus natural gelatin, chondroitine sulfate or polyethylene glycol as solvent(s). The mass ratio is 20-80:80-20. The spinning solution accounts for 3-15% of total weight. In blending, the solution of hydrophilic polymer can be added with a solution of basic fibroblast factor, and make the concentration of cytokine of 0.001-0.5%.

A medicine added in blending or bio-printing can choose, in accordance with the actual situation, antibiotic or drug for hemostasis or anti-adhesion. In the transplantation of dura mater due to tumor excision, the drugs for chemotherapy of brain tumor can be added.

An antibiotic includes but not limited to the cephalosporin, ampicillin, spiramycin, sulfonamides and quinolones. The first choice is ceftriaxone sodium. As meninges surgeries often need to open the skull and at present, the intracranial infection is often bacterial mainly comprising staphylococcus aureus, streptococcus, pneumococcus, *escherichia coli, salmonella* and *pseudomonas aeruginosa*. The commonest virus is *staphylococcus aureus*. According to the clinical reports, the ceftriaxone sodium offers better therapy effect.

The anti-tumor medicine includes but not limited to nimustine, semustine, liposome doxorubicin, dactinomycin D and vincristine. The vincristine is first choice.

A medicine for hemostasis or anti-adhesion can speed up the healing of wound and prevent the occurrence of adhesion. Such medicine includes but not limited to the hemostasis factor (which makes the material own the function of hemostasis), the inhibitor of collagen synthase (such as tranilast and pemirolast, which inhibit the revival of collagen), the anti-coagulation drug (such as dicoumarolum, ehparin sodium and hirudin), the anti-inflammatory drug (such as promethazine, dexamethasone, hydrocortisonum, prednisolone, ibuprofen and oxyphenbutazone), the calcium channel blocker (such as diltiazem hydrochloric, nifedipine and verapamil hydrochloride), the cell growth inhibitor (such as fluorouracil), the hydrolase (such as hyaluronidase, streptokinase, urokinase, pepsin and tPA) and the oxidation reductant (such as methylene blue).

According to an embodiment of the invention, in blending, the electrospinning solution is added with a cytokine and/or a medicine in this formula: the basic fibroblast growth factor accounting for 0.001-0.05% of electrospinning solution weight, the ampicillin accounting for 3% of electrospinning solution weight, the hemostasis factor accounting for 0.001-0.05% of electrospinning solution weight. In a meninges restoration operation due to brain tumor, the nimustine accounting for 0.01-5% of the weight can be added.

The obtained artificial dura mater should be rinsed, sterilized, packaged and stored.

Example 1

Poly(L-lactide) (PLLA) and ε-caprolactone, in the mass ratio of 50:50 and with number-average molecular weight of 260,000, are dissolved into a solvent of hexafluoro isopropyl alcohol to form a hydrophobic electrospinning solution. Put the solution into the sprayer of electrospinning. The micro-injection pump is operated at a velocity of 5 milliliter/hour; the high voltage generator is operated at a voltage of 30 kilovolts and a receiving distance of 20 centimeters. The fibers are received to form a membrane structure and have a diameter in the average of 300 nm. After the receiving process is completed, the spinning device is closed.

The artificial dura mater acquired is rinsed for five times with ethyl alcohol and distilled water. The dura mater, then, is packaged in vacuum after freeze dry. After sterilization with 25 kGy cobalt-60, the dura mater is stored at minus 20° C.

Example 2

The preparing method is the same as which of the example 1.

The hydrophilic solution for electrospinning choose poly ethanedioic acid and chondroitine sulfate, in the mass ratio of 70:30 and the mass fraction of spinning liquid is 9%.

The electrospinning device is activated, and a hydrophilic electrospun layer is formed on the hydrophobic layer already formed in Embodiment 1. The receiving distance is 11 centimeters, the voltage is 20 kilovolts, and the acquired hydrophilic layer comprises fibers in the average with a diameter of 10 μm.

The rinse and store are the same as those in Embodiment 1.

Example 3

The hydrophobic electrospun layer is prepared in the same manner with that in Embodiment 1.

The transition layer adopts a polymer solution of polyurethane and hyaluronic acid in the mass ratio of 70:30 and has a mass fraction of 10%. The spinning is activated with a receiving distance of 11 centimeters and a voltage of 20 kilovolts. The fibers have a diameter at average of 5 μm. On the hydrophobic layer, the transition layer is made.

Then, on the transition layer, the hydrophilic layer is spun, in the same manner as that in Example 4. After that, the spinning is stopped.

The rinse and store are the same as them in Example 1.

Example 4

(1) prepare the hydrophobic electrospun layer: Choose the hydrophobic polycaprolactone and a mixed solvent of chloroform or methyl alcohol in a ratio of 1:1. Add with ceftriaxone sodium, at a concentration of 1%. Get the uniform solution.

Add the above solution into the sprayer for electrostatic spinning, and perform the electrospinning with a micro-injection pump operated at a velocity of 0.8 milliliters/hour and a high voltage generator operated at a voltage of 12 kilovolts and with a receiving distance of 15 centimeters. Obtain the fibers in membrane structure. The fibers of the hydrophobic electrospun layer have a diameter of 600 nanometers.

Close the spinning device.

(2) prepare the hydrophilic electrospun layer: Adopt the hydrophilic silk protein and natural gelatin in the ratio of 20-80:80-20 and have the mass fraction of spinning liquid at 9%.

Prepare the solution of basic fibroblast factor. Mix the solution with the above mentioned electrospinning solution evenly, and have the final concentration of cytokine to be 0.001%, the receiving distance to be 10 cm, and the voltage to be 20 KV. Start the electrospinning, and form the hydrophilic layer on the hydrophobic layer formed already. The average diameter of fibers from the hydrophilic layer is in the level of micron.

The rinse and store are the same as them in Example 1.

Example 5

(1) prepare the hydrophobic electrospun layer: Select the hydrophobic polycaprolactone and a mixed solvent of chloroform and methyl alcohol in ratio of 1:1. Blend with vincristine at the concentration of 100 ng/ml, and get the uniform solution.

Add the above solution into the sprayer for electrospinning, adjust the velocity of micro-injection pump to be 0.8 ml per hour, the voltage of high voltage generator to be 12 KV, and the receiving distance of receiving device to be 15 cm, and obtain the fibers in membrane structure. The fibers of the hydrophobic electrospun layer have a diameter of 600 nanometers.

Close the spinning device.

(2) prepare the transition layer: Choose polyurethane and hyaluronic acid in the mass ratio of 70:30. Have the mass fraction of spinning solution at 10%. Blend with ampicillin at concentration of 3%. The uniform solution is form.

Start the spinning. Spin the transition layer on the hydrophobic layer already formed.

The receiving distance is 11 centimeters, the voltage is 20 kilovolts, and the average diameter of fibers is 5 μm.

Close the spinning device.

(3) prepare the hydrophilic electrospun layer: Adopt the hydrophilic silk protein and natural gelatin in the ratio of 20-80:80-20 and have the mass fraction of spinning solution at 9%. Blend with ampicillin solution at a final concentration of 3%.

Activate the spinning device, adjust the receiving distance to be 10 cm, and spin the hydrophilic layer on the transition layer already formed. The average diameter of fibers should be in the level of micron.

The rinse and store are the same as them in Example 1.

Example 6

(1) prepare the hydrophobic electrospun layer with bio-printing:

The hydrophobic solution selects the hydrophobic poly(L-lactide) (PLLA) and ϵ-caprolactone, in a mass ratio of 50:50, as copolymer with a number-average molecular weight of 260000, dissolved into the hexafluoro isopropyl alcohol.

The cross-linking agent selects 0.1M calcium chloride solution.

The hydrogel containing a cytokine adopts an alginate solution of hemostasis factor. The hemostasis factor has a concentration of 10 ppm in mass in the cytokine alginate solution.

The solution with 0.1 M calcium chloride should be placed into the cell petri dish with a diameter of 150 mm. The co-receiver share by the spinning device and bio-printing is placed into the petri dish. In forming of an electrospun layer, the receiving device should contact with the solution in petri dish. The printer head is fixed below the electrospinning needle which is inside the spinning device box, which offers a function of fixed-point print on specific area with hemostasis factor. The prepared cytokine alginate solution is put into the cartridge of jet printer. In this embodiment, the cartridge is HP51626A.

The hydrophobic electrospinning solution is placed into the sprayer for spinning. After that, adjust the velocity of micro-injection pump to be 5 milliliters/hour, the voltage of high voltage generator to be 30 kilovolts, and the receiving distance of receiving device to be 20 centimeters. The fiber is received in membrane structure. The spinning lasts for 20 minutes before the spinning device is closed.

The hydrogel solution containing the cytokine is printed on the nano-bionic scaffold with jet printer. Once the hydrogel is solidified, the hydrophobic electrospun layer with cytokine by bio-printing is acquired.

(2) prepare the hydrophilic electrospun layer with bio-printing:

An electrospinning solution, a hydrogel solution with medicine and the cross-linking agent solution are prepared.

Polyglycol and chondroitine sulfate, as hydrophilic materials, in the mass ratio of 70:30 are chosen. The spinning solution has the mass fraction of 9%. The cross-linking agent solution is the 0.1M calcium chloride solution.

The hydrogel solution containing a cytokine adopts the alginate solution with basic fibroblast factor. The basic alginate solution has the basic fibroblast factor at the concentration of 100 ppm.

The parameters are set as follows: Adjust the velocity of micro-injection pump to be 0.8 milliliters/hour, the voltage of high voltage generator to be 20 kilovolts and the receiving distance of receiving device to be 11 centimeters. Other preparing procedures are the same as those in first step above. After the hydrophilic fiber is received in membrane structure, by bio-printing, the hydrogel solution containing the basic fibroblast factor is printed to the nano-bionic scaffold. Once the hydrogel is solidified, the hydrophilic electrospun layer with cytokine by bio-printing is acquired.

The rinse and store are the same as those in Example 1.

Example 7

(1) The preparation of hydrophobic electrospun layer with bio-printing is the same as described in Example 6.

(2) prepare the transition layer by bio-printing

The electrospinning liquid solution of transition layer is comprises the polyurethane and the hyaluronic acid in the mass ratio of 70:30. The mass fraction of the spinning solution is 10%. The blended ampicillin is in the concentration of 3%.

The cross-linking agent solution is the 0.1 M calcium chloride solution.

The hydrogel solution with cytokine is an alginate solution of hemostasis factor, and the mass percentage of the hemostasis factor is 10 ppm.

The parameters are adjusted in this way as follows: The velocity of micro-injection pump is 4 milliliters/hour, the voltage of high voltage generator is 20 kilovolts, and the receiving distance is 11 centimeters. The other procedures are the same as the above procedures. The fiber is received in membrane structure. The hydrogel solution containing the cytokine will be printed on the transition layer. After the hydrogel is solidified, the hydrophobic electrospun layer with cytokine by bio-printing is obtained.

(3) The preparation of hydrophilic electrospun layer with bio-printing is the same as described in Example 6.

The rinse and store are the same as those described in Example 1.

Experimental Example 1

The dura mater obtained from Example 1 is applied to dog for the animal experiment, while the control is a commercialized, clinical applicable heterogenic meninges repairing product. Three healthy dogs are chosen, either male or female, in the weight between 10 and 15 kg, and under observation for two to three months. The dogs chosen in the experiment are under general anesthesia. Their skulls are opened at both left and right sides. Their dura maters are surgically removed, and the defects of dura maters and injuries of brain tissue appear. Then, the dura maters obtained from the Embodiment 1 and the control, respectively, are implanted for repairing the dural defects at the left and right sides of the dog's brain. After operation, the dogs are feed normally as usual and observed periodically. The specimen is taken from the implanted area at the end of each observation period. In the end of the observation period, the skulls of the dogs are exposed by the way described above after general anesthesia. Expose and separate the outer surface of the repairing material. To retrieve the samples, these dogs are sacrificed by administration of an intravenous injection of air. The skulls are opened surgically. The implants and surrounding tissue are taken out. The retrieved samples are inspected carefully with details including the appearance, characters, its relation to the surroundings cyst, callosity, as well as the adhesion between its inner surface and brain tissue. The specimen is stored in a bottle and treated and fixed with Formalin solution. Label the bottle. One week later, take out a local tissue; embed with paraffin section and histological stain with HE.

Several days after implantation, the three dogs recover well, and incisions are healed well with no obvious secretion. The dogs eat and drink normally as well as their outdoor activities are normal without any obvious movement malfunction. Three months post-implantation, the three dogs are sacrifice by an intravenous injection of air. After sacrifice, taking the surgical site as center, the specimen is cut from one centimeter outer the operation site, and it includes the repair material, the surrounding dura mater and part of brain tissue. After the specimen is taken, separate the skull and meninges in order. It is found that the meninges, where dura mater transplanted, are formed completely; the transplanted material has been replaced by fibrous tissue, and has connected tightly with the native meninges without border. The internal surface of the newly-formed meninges at transplantation site is free from adhesion with the brain tissue, and the surface of corresponding brain tissue is smooth and free from adhesion to the implant. While, in the implanted site of the control samples, the transplanted material has not yet degraded and exist a few of adhesion at the transplantation site to the internal surface of meninges.

Experimental Example 2

The dura mater prepared in the Example 2 is now applied for the dog experiment. Five dogs are in weight of 15-20 kg, 1.5-2-year-old, and either male or female. They are in general anesthesia through the intramuscular injection of ketamine. After anesthesia and shave, the animals are placed on the operation table in lateroabdominal position. The disinfection is made with 2% iodine and 75% alcohol. The animals' heads are opened surgically in lengthwise direction. Stripper is used to separate the periosteum of the skull, and the two top skull plateaus are exposed. The high-speed driller is used to open the skull. The two skull windows at vertex are formed, and two rectangular dura maters in size of 3 cm×3 cm at the top of head are cut off with the scissors. Finally the top dura mater defects are made for the following implantation with artificial dural mater and control. On the exposed brain surface, the electrocoagulation is applied to make 6 injury points in the size of 1 mm×1 mm. Then, the artificial dura mater manufactured in Embodiment 2 is trimmed to the same shape and size as those of the dural defect and loaded into the defect. The hydrophobic layer is toward the brain surface, and the sutures is made with the 4/0 thread in the interval of 4 mm, to repair the dural defect of dogs. The round needle and 4/0 thread are used for suture of muscle. The commercialized, clinically applicable, animal material based dural repair product is applied as a control. After operation, the dogs are feed normally as usual and observed periodically. The animals recover well, and incisions are healed well. No obvious leakage of cerebrospinal fluid or occurrence of epilepsy is found. The dogs eat and drink normally as well as their outdoor activities are normal without any obvious movement malfunction, and they survive to the expected longevity.

Eighteen months post-implantation, the dogs are sacrificed and the specimen is taken at the surgical site, and it includes the artificial dura mater, the surrounding dura mater, and part of the surrounding brain tissue. After carefully observe the specimen, we can see that the connection between the artificial dura mater and native dura mater is tight and smooth, without clear boundary, healed well, besides, and with thread seen only. The native dura mater does not show any hyperaemia, hemorrhage or other rejection reaction. While, the results of the control show that the implant material is not yet degraded, and at the implanted site, the inner surface of meninges adheres to brain tissue to some degree.

Experimental Example 3

The artificial dura mater obtained from Example 3 is now under the experiment with New Zealand rabbit.

The animals under experiment are opened in the skulls, and the defect of dura mater and injury of brain tissue are made surgically. Then, the artificial dura mater is used to repair the defect. After the operation, the rabbits are feed normally as usual and observed periodically. These animals recover well. Eighteen months post-implantation, the rabbits are sacrificed and the specimen is taken at the surgical site. The specimen includes the artificial dura mater, surrounding dura mater and part of the surrounding brain tissue. When observe the specimen carefully, it is seen that the epithelial cells cover the inner surface of the dura mater; under the epithelium, fibrous tissue is formed, fibroblast progenitor cells proliferate, and collagen fibers are increased. All of these result in the formation of new vascularized tissues, in-growth of native dura mater, degradation of the implant material, deduction of total mass of the implant, and generation of rich capillary networks. In the interface of old and new tissues, no neutrophil, lymphocyte or other cell reaction for inflammation is found, and no cyst wall is formed. The arachnoid mater and brain tissue are normal.

Experimental Example 4

The dura mater obtained from Example 4 is now applied to the dog experiment, and the method is the same as Experimental example 2.

Fifteen months post-implantation, the dogs are sacrificed and the specimen is taken at the surgical site. The specimen includes the artificial dura mater, surrounding dura mater, and part of the surrounding brain tissue. After carefully observe the specimen, it is seen that the connection between the artificial dura mater and native dura mater is tight and smooth, without clear boundary, completed cured, and with thread seen only. The native dura mater does not show hyperaemia, hemorrhage or other rejection reaction.

Experimental Example 5

The dura mater obtained from Example 5 is now applied to the New Zealand rabbit experiment, and the control is the commercialized, clinically applicable, animal materials based dura mater product as the repair material.

The method is the same as Experimental example 3. Fifteen months post-implantation, the rabbits are sacrificed and the specimen is taken at the surgical site. When observe the specimen carefully, it is seen that the epithelial cells cover the inner surface of the dura mater; under the epithelium, fibrous tissue is formed, fibroblast progenitor cells proliferate, and collagen fibers are produced. All of these result in the formation of new vascularized tissues, in-growth of native dura mater, degradation of the implant material, deduction of total mass of the implant, and generation of rich capillary networks. In the interface of old and new tissues, no neutrophil, lymphocyte or other cell reaction for inflammation is found, and no cyst wall is formed. The arachnoid mater and brain tissue are normal. While, the results with the control show that the implant material is not yet degraded, and at the implanted site, the inner surface of meninges adheres to brain tissue to some degree.

Experimental Example 6

The dura mater obtained from Example 6 is now applied to the dog experiment, and the method is the same as Experimental example 2.

Twelve months post-implantation, the dogs are sacrificed and the specimen is taken at the surgical site. The specimen includes the artificial dura mater, surrounding dura mater, and part of the surrounding brain tissue. When observe the specimen carefully, it is seen that the connection between the artificial dura mater and native dura mater is tight and smooth, without clear boundary, completed cured, and with thread seen only. The native dura mater does not show hyperaemia, hemorrhage or other rejection reaction.

Experimental Example 7

The dura mater obtained from Example 7 is now applied to the New Zealand rabbit experiment.

The method is the same as Experimental example 3. Twelve months post-implantation, the rabbits are sacrificed and the specimen is taken at the surgical site. When observe the specimen carefully, it is seen that the epithelial cells cover the inner surface of the dura mater; under the epithelium fibrous tissue is formed, fibroblast progenitor cells proliferate, and collagen fibers are increase. All of these result in the formation of new vascularized tissues, in-growth of native dura mater, degradation of the implant material, deduction of total mass of the implant, and generation of rich capillary networks. In the interface of old and new tissues, no neutrophil, lymphocyte or other cell reaction of inflammation is found, and no cyst wall is formed. The arachnoid mater and brain tissue are normal.

Notwithstanding the embodiments have been given and described, the person skilled in the field can, without deviation from the principle and theory, can make the variation, modification, replacement and change of these embodiments, as given in the invention scope and right claims.

The invention claimed is:

1. A method of treating a subject having a defective dura mater, comprising implanting an artificial dura mater proximate to said defective dura mater in the brain of said subject, wherein said artificial dura mater consists essentially of synthetic materials and comprises at least a hydrophobic and biodegradable electrospun layer comprising 30% polylactic acid (PLA), and wherein said hydrophobic electrospun layer comprises fibers with a diameter of 50-1000 nM and pores with a size of less than 3 μM.

2. The method according to claim 1, wherein said artificial dura mater further comprises at least a hydrophilic electrospun layer disposed on said hydrophobic electrospun layer.

3. The method according to claim 2, wherein said hydrophilic electrospun layer is prepared, by a method comprising electrospinning, with one or more hydrophilic polymers selected from the group consisting of chondroitine sulfate, heparin, agar, glucan, algin, modified cellulose, alginate, starch, cellulose, gelatin, fibrinogen, silk protein, elastin-mimicry peptide polymer, collagen, chitosan, modified chitosan, hydrophilic polyurethane, polyethylene glycol, polymethylmethacrylate, poly(3-hydroxybutyrate-co-3-hydroxyvalerate) (PHBV), poly(3-hydroxybutyrate-co-3-hydroxyhexanoate) (PHBHHx), polyvinyl alcohol, polylactide and mixtures thereof.

4. The method according to claim 2, wherein said artificial dura mater further comprises a transition layer disposed between the hydrophobic and hydrophilic electrospun layers, wherein said transition layer has hydrophilicity that gradually increases from the side proximate to said hydrophobic electrospun layer to the side proximate to said hydrophilic electrospun layer.

5. The method according to claim 1 or 2, wherein said artificial dura mater further comprises a cytokine and/or a medicine that is adhered to said hydrophobic electrospun layer and/or said hydrophilic electrospun layer.

6. The method according to claim 5, wherein said cytokine is selected from the group consisting of interleukin, colony stimulating factor, tumor necrosis factor, platelet derived growth factor, basic fibroblast growth factor and combinations thereof.

7. The method according to claim 5, wherein said medicine is one or more selected from the group consisting of an antibiotic, a hemostat, an anti-adhesion agent and an anti-tumor drug.

8. The method according to claim 5, wherein said cytokine and/or medicine is enclosed in a hydrogel.

9. The method according to claim 8, wherein said hydrogel comprises one or more selected from the group consisting of polysaccharide polymer, polypeptide polymer and synthetic hydrophilic high molecular polymer.

10. A method of treating a subject having a defective dura mater, comprising implanting an artificial dura mater proximate to said defective dura mater in the brain of said subject, wherein said artificial dura mater consists essentially of synthetic materials and comprises at least a hydrophobic and biodegradable electrospun layer comprising 50% polylactic acid, and wherein said hydrophobic electrospun layer comprises fibers with a diameter of 50-1000 nM and pores with a size of less than 3 μM.

11. The method of claim 10, wherein said biodegradable electrospun layer comprises 50% polylactic acid and 50% ε-caprolactone.

* * * * *